US00PP33313P2

(12) United States Plant Patent
Van Swieten

(10) Patent No.: US PP33,313 P2
(45) Date of Patent: Aug. 3, 2021

(54) ***PHALAENOPSIS* ORCHID PLANT NAMED 'PHALHAKAK'**

(50) Latin Name: ***Phalaenopsis* hybrid**
Varietal Denomination: PHALHAKAK

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/974,412

(22) Filed: Jan. 20, 2021

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALHAKAK', particularly characterized by light reddish-purple flowers with small centers and light red-purple lips, a flat flower shape in lateral view, a concave lateral sepal shape in cross section, and is propagated by meristem tissue culture, is disclosed.

3 Drawing Sheets

Genus and species: *Phalaenopsis* hybrid.
Variety denomination: 'PHALHAKAK'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALHAKAK'.

The new *Phalaenopsis* plant is a product of a planned breeding program conducted by the inventor in Bleiswijk, the Netherlands. The objective of this breeding program was to create a new *Phalaenopsis* plant with light reddish-purple flowers with small centers and light red-purple lips, suitable for potted plant production.

The new *Phalaenopsis* plant 'PHALHAKAK' is a result of cross-pollination made by the inventor in September 2010 in Bleiswijk, the Netherlands, of the proprietary female, or seed parent, *Phalaenopsis* hybrid '22791-01' (unpatented) with the proprietary male, or pollen parent, *Phalaenopsis* hybrid '01-1988' (unpatented).

The new *Phalaenopsis* was selected by the inventor as a single plant within the progeny of the stated cross-pollination in a controlled greenhouse in Bleiswijk, the Netherlands, in August 2013. Asexual reproduction of the new *Phalaenopsis* plant by meristem tissue culture since 2014 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Aug. 30, 2019 (Application no. 2019/2063), by Applicant who obtained the subject matter disclosed directly from the inventor. 'PHALHAKAK' has not been made publicly available or sold anywhere in the world prior to the effective filing date of this application with the exception of sales or disclosures made one year or less before the effective filing date of this claimed invention by Applicant who obtained 'PHALHAKAK' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALHAKAK' as a new and distinct variety of *Phalaenopsis* plant:

1) Light reddish-purple flowers with small centers and light red-purple lips;
2) Flower shape in lateral view is flat; and
3) Lateral sepals shape in cross section is concave.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 50-week-old plants in November 2020. Colors in the photographs may differ from the color values cited in the detailed botanical description, which accurately describe the actual colors of the new variety.

DESCRIPTION OF THE NEW VARIETY

Figure 1:
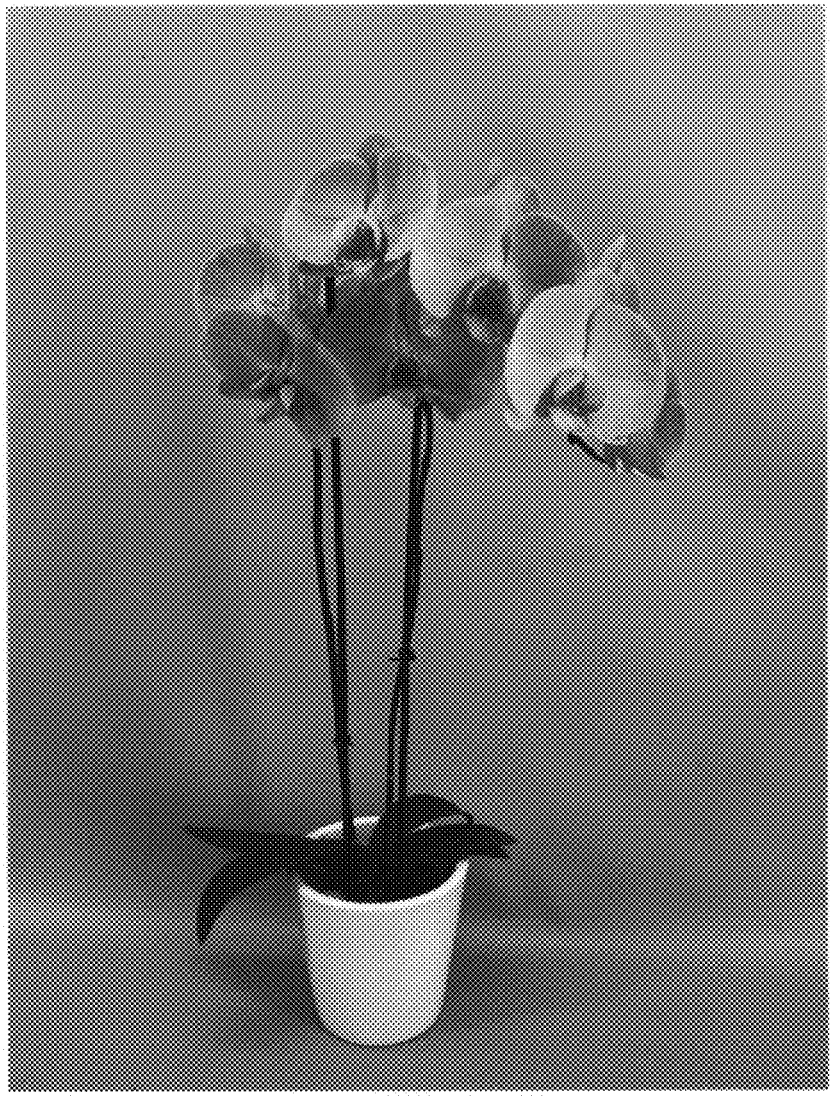
FIG. 1 shows the overall plant habit, including blooms and foliage of 'PHALHAKAK'.
Figure 2:
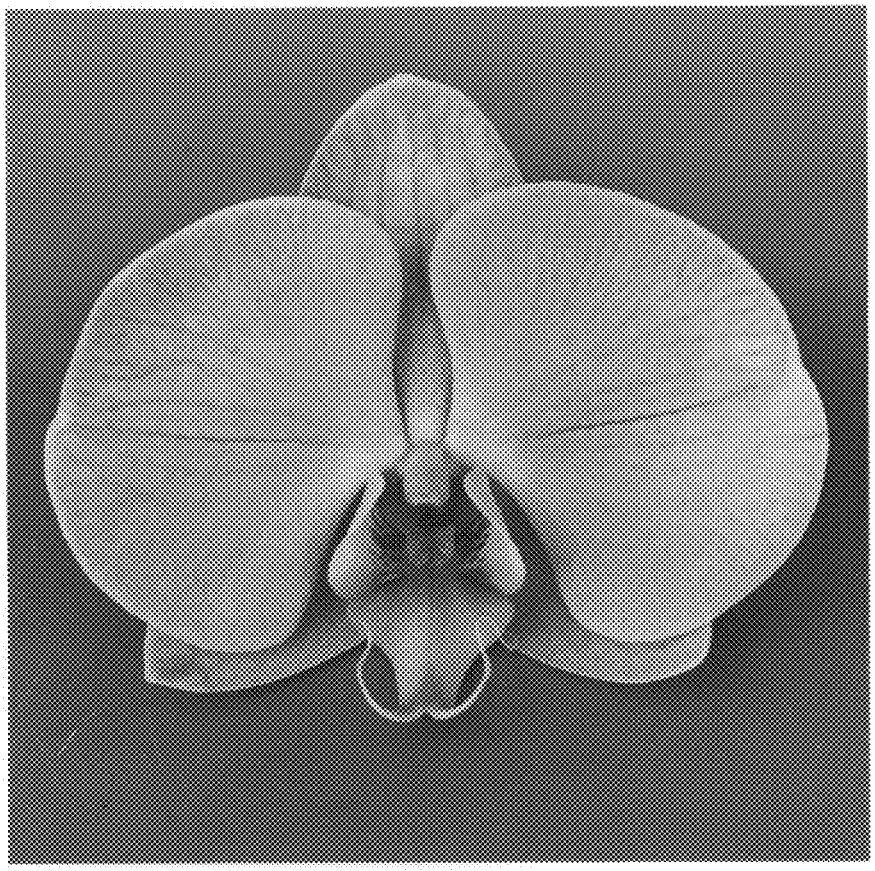
FIG. 2 shows a close-up of a flower of 'PHALHAKAK'.
Figure 3:
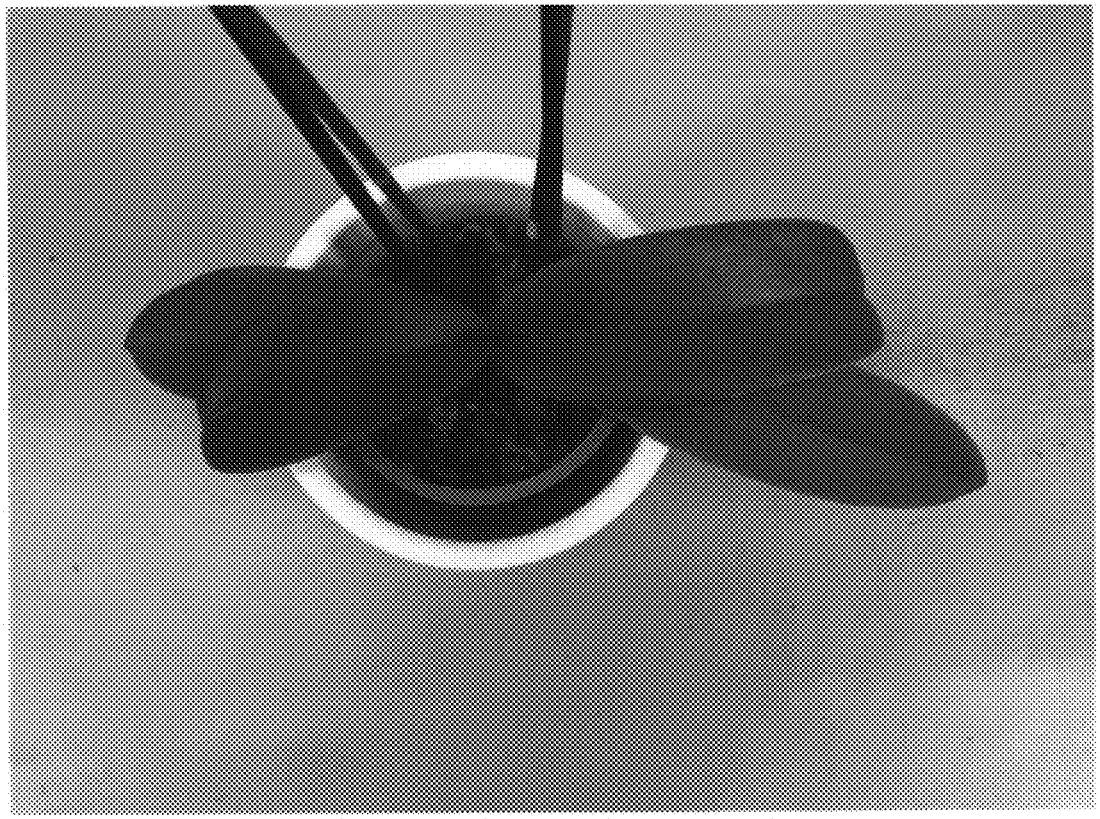
FIG. 3 shows an overhead view of the leaves of 'PHALHAKAK'.

The following detailed description sets forth the distinctive characteristics of 'PHALHAKAK'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in November 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALHAKAK'.

Parentage:

*Female parent*.—*Phalaenopsis* cultivar '22791-01' (unpatented).

*Male parent*.—*Phalaenopsis* cultivar '01-1988' (unpatented).

Propagation:

*Type*.—Meristem tissue culture.

Roots:

*Root description*.—Greyed-green (a color in between RHS 190B and 190C) colored roots with branching lateral roots having yellow-green (RHS 144B) with a hint of purplish-red (RHS N77B) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height* (*from soil level to top of inflorescence*).—Approximately 62.0 cm to 67.0 cm.

*Width* (*measured from leaf tips*).—About 35.0 cm to 37.0 cm.

*Vigor*.—Strong.

Leaves:

*Mature leaves*.—Quantity per plant: 6 to 7 leaves are produced before flowering. Length (fully expanded): 16.0 cm to 19.0 cm. Width: 6.0 cm to 7.0 cm. Position of the broadest part of the leaf: At the middle. Shape: Oblong. Base shape: Moderately elongated. Apex: Unequal obtuse. Leaf blade angle with the petiole (measured from the horizontal position): Between 10 degrees and 25 degrees. Leaf margin: Entire. Color: Upper surface: RHS 147A. Lower surface: RHS 147B. Texture (both upper and lower surfaces): Smooth. Thickness: 2.0 mm to 3.0 mm. Variegation: Absent. Venation: Pattern: Parallel. Color of the midvein: Upper surface: RHS 147A. Lower surface: RHS 146A.

Peduncle:

*Quantity per plant*.—1 to 2.

*Number of flowers per peduncle*.—7 to 10.

*Length*.—62.0 cm to 67.0 cm.

*Diameter*.—5.0 mm to 6.0 mm.

*Strength*.—Strong.

*Aspect*.—Upright to slightly pendent.

*Texture*.—Smooth.

*Color*.—Yellow-green (RHS 146C) with a touch of reddish-brown (RHS 200B).

*Internode length*.—4.0 cm to 5.0 cm.

Inflorescence description:

*Appearance*.—Upright to slightly pendent, raceme inflorescence with bilaterally symmetrical flowers that open in succession beginning with the lowermost flower.

*Number of inflorescences*.—1 to 2.

*Inflorescence size*.—Height (from base to tip): 210.0 mm to 260.0 mm.

*Flowering time*.—First flowers can be expected 10 to 11 months after planting in a 12-cm pot.

*Flower*.—Height: 80.0 mm to 85.0 mm. Diameter: 100.0 mm to 105.0 mm. Depth of lip: 26.0 mm to 28.0 mm.

*Flower longevity*.—On the plant: 18 to 20 weeks.

*Flower shape*.—Flat.

*Fragrance*.—Absent.

*Flower bud*.—Average size: Large. Length: 25.0 mm to 27.0 mm. Width: 20.0 mm to 22.0 mm. Shape: Egg shaped. Color: Hint of yellow-green (RHS 146D) at the base; mix of purplish-red (RHS N77B) and dark purplish-red (RHS N79C) toward the tip.

*Petals*.—Arrangement: Open/free. Shape: Semi-circular. Apex: Emarginated asymmetric. Margin: Weakly undulated. Length (from base to tip): 45.0 mm to 47.0 mm. Width: 63.0 mm to 65.0 mm. Position of the broadest part of the petal: Toward the base. Color (when fully opened): Upper surface: Basic color: Light reddish-purple (RHS N78D). Over color: Touch of very light purple (RHS 76C) at the base; reddish-purple midvein (RHS N78B) and reddish-purple stripes (a color in between N78B and N78C); purplish-pink shade (RHS N78C). Lower surface: Basic color: Light reddish-purple (a color in between RHS 76A and N78D). Over color: Purplish-pink stripes (RHS N78D). Number of spots and stripes on the petals (upper surface): Medium stripes. Color of spots and stripes on the petals (upper surface): RHS N78C. Density of netting of the petals (upper surface): None. Color of the netting (upper surface): Not applicable.

*Dorsal sepal*.—Shape: Elliptic. Apex: Obtuse symmetric. Margin: Entire. Length (from base to tip): 49.0 mm to 51.0 mm. Width: 34.0 mm to 36.0 mm. Position of the broadest part of the dorsal sepals: At the middle. Color (when fully opened): Upper surface: Basic color: Light reddish-purple (RHS N78D). Over color: Hint of white (RHS NN155C) at the base; purplish-pink stripes (RHS N78C) and purplish-pink margin (RHS N78C). Lower surface: Basic color: Light reddish-purple (a color in between RHS N78C and N78D). Over color: Light yellow-green (RHS 145C) at the base. Number of spots and stripes on the dorsal sepals (upper surface): Medium stripes. Color of spots and stripes on the dorsal sepals (upper surface): RHS N78C. Density of netting of the dorsal sepals (upper surface): Low. Color of the netting: RHS N78C.

*Lateral sepals*.—Shape: Ovate. Apex: Obtuse symmetric. Margin: Entire. Length (from base to tip): 50.0 mm to 52.0 mm. Width: 30.0 mm to 32.0 mm. Position of the broadest part of the lateral sepals: At the base. Color (when fully opened): Upper surface: Basic color: Light purple (RHS 76A). Over color: Light yellow-green (RHS 145C) at the base; light reddish-purple stripes and margin (RHS N78D). Lower surface: Basic color: Light reddish-purple (RHS N78D). Over color: Light yellow-green (RHS 145C) at the base. Number of spots and stripes on the lateral sepals (upper surface): Medium stripes. Color of spots and stripes on the lateral sepals (upper surface): RHS N78D. Density of netting of the lateral sepals (upper surface): Low. Color of the netting (upper surface): RHS N78C.

*Labellum* (*lip*).—Whiskers: Present. Length of whiskers: 26.0 mm to 28.0 mm. Color of whiskers: Light reddish-purple (RHS N78D) at the base with light greenish-yellow tips (RHS 8C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 22.0 mm to 24.0 mm. Width: 15.0 mm to 17.0 mm. Color: Upper surface: Red stripes (a color in between RHS 178B and 178C) at the base; yellow (RHS 13A) at the base toward margin on both sides; white (RHS NN155C); shaded (RHS 76A) with purplish-pink margin (RHS N78D) toward the tip. Lower surface: Touch of dark reddish-orange (RHS 186C) at the base; yellow (RHS 13B) on sides; white (RHS NN155C); shaded (RHS N78D) toward the tip. Number of spots and stripes on the lateral lobe: Few stripes and spots at the base. Color of spots and stripes on the lateral lobe: A color in between RHS 178B and 178C. Density of netting of the lateral lobe: None. Color of the netting: Not applicable.

*Apical lobe*.—Shape: Triangular. Margin: Entire. Length: 22.0 mm to 24.0 mm. Width: 22.0 mm to 24.0 mm. Color: Upper surface: Dark reddish-orange margin (RHS 178B) at the base; yellow base and wings (RHS 13B); light purple (RHS 76A) and light reddish-purple (RHS N78D) toward whiskers. Lower surface: Dark reddish-orange margin (RHS 178B) at the base; yellow wings (RHS 13C); light reddish-purple (RHS N78D) toward whiskers. Number of spots and stripes on the apical lobe: None. Color of spots and stripes on the apical lobe: Not applicable. Density of netting of the apical lobe: None. Color of the netting: Not applicable.

*Callus*.—Average size: Medium to large. Height: 8.0 mm to 9.0 mm. Length: 6.0 mm to 7.0 mm. Width: 4.0 mm to 5.0 mm. Color: Orange-yellow (RHS 17A); dotted (RHS 178A).

Reproductive organs:

*Column*.—Length: 9.0 mm to 11.0 mm. Diameter: 5.0 mm to 6.0 mm. Color: Very light purple (RHS 76C) with light reddish-purple tip (RHS N78D).

*Pollinia*.—Quantity: 2. Diameter: 0.9 mm to 1.1 mm. Color: Orange (RHS 24A).

*Ovary*.—Length: 9.0 mm to 11.0 mm. Diameter: 2.2 mm to 2.5 mm.

*Pedicel*.—Length: 35.0 mm to 37.0 mm. Diameter: 2.6 mm to 2.9 mm. Texture: Smooth. Color: Yellow-green (RHS 146C) with a hint of reddish-brown (RHS 200B) at the base; light purple (RHS 75B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALHAKAK' differs from the female parent plant '22791-01' (unpatented), in that 'PHALHAKAK' has flowers with a main color of light reddish-purple, apical lobes with a main color of light reddish-purple, and whiskers that are light reddish-purple at the base with light greenish-yellow tips, whereas '22791-01' has flowers with a main color of reddish-purple, apical lobes with a main color of purplish-red, and whiskers that are purplish-red with light yellow and white toward the tips.

'PHALHAKAK' differs from the male parent plant '01-1988' (unpatented) in that 'PHALHAKAK' has flowers with a main color of light reddish-purple and whiskers that are light reddish-purple at the base with light greenish-yellow tips, whereas '01-1988' has flowers with a main color of white and whiskers that are white with yellow tips. Additionally, 'PHALHAKAK' has smaller flowers than '01-1988'.

'PHALHAKAK' is most similar to the commercial *Phalaenopsis* plants named 'PHALGANZI' (U.S. Plant Pat. No. 31,760) and 'PHALGORYQ' (U.S. Plant Pat. No. 31,050). 'PHALHAKAK' differs from the commercial variety 'PHALGANZI' in that 'PHALHAKAK' has very light purple columns with light reddish-purple tips and emarginated petal apexes, whereas 'PHALGANZI' has white columns with a light purple region in the middle and rounded to slightly emarginated petal apexes. Additionally, 'PHALHAKAK' has smaller flowers and narrower petals than 'PHALGANZI'.

'PHALHAKAK' differs from the commercial variety 'PHALGORYQ' in that 'PHALHAKAK' has obtuse dorsal sepal apexes and emarginated petal apexes, whereas 'PHALGORYQ' has slightly emarginated dorsal sepal apexes and rounded petal apexes. Additionally, 'PHALHAKAK' has smaller flowers and wider petals than 'PHALGORYQ'.

I claim:

1. A new and distinct variety of *Phalaenopsis* plant named 'PHALHAKAK', substantially as described and illustrated herein.

* * * * *